United States Patent
Paulus et al.

(10) Patent No.: US 9,234,875 B2
(45) Date of Patent: Jan. 12, 2016

(54) SIMULTANEOUS PURIFICATION OF CELL COMPONENTS

(71) Applicants: Bio-Rad Laboratories, Inc., Hercules, CA (US); Technion Research & Development Foundation Ltd., Technion, Haifa (IL)

(72) Inventors: Aran Paulus, San Jose, CA (US); Camille Diges, Concord, CA (US); Roumen Bogoev, Hercules, CA (US); Sricharan Bandhakavi, Albany, CA (US); Annett Hanh-Windgassen, Sunnyvale, CA (US); Anton Posch, Grafting (DE); Elad Brod, Tivon (IL); Uri Sivan, Haifa (IL)

(73) Assignees: BIO-RAD LABORATORIES, INC., Hercules, CA (US); TECHNION RESEARCH & DEVELOPMENT FOUNDATION LTD., Haifa (IL)

( * ) Notice: Subject to any disclaimer, the term of this patent is extended or adjusted under 35 U.S.C. 154(b) by 524 days.

(21) Appl. No.: 13/669,012

(22) Filed: Nov. 5, 2012

(65) Prior Publication Data

US 2013/0126356 A1    May 23, 2013

Related U.S. Application Data

(60) Provisional application No. 61/555,689, filed on Nov. 4, 2011, provisional application No. 61/555,708, filed on Nov. 4, 2011.

(51) Int. Cl.
*G01N 27/447* (2006.01)
*G01N 27/453* (2006.01)
*C07K 1/28* (2006.01)

(52) U.S. Cl.
CPC ............ *G01N 27/44795* (2013.01); *C07K 1/28* (2013.01); *G01N 27/453* (2013.01)

(58) Field of Classification Search
CPC ... G01N 27/44795; C07K 1/28; B01D 15/168
See application file for complete search history.

(56) References Cited

U.S. PATENT DOCUMENTS

| | | | |
|---|---|---|---|
| 4,396,477 | A | 8/1983 | Jain |
| 4,868,130 | A | 9/1989 | Hargreaves |
| 4,880,513 | A | 11/1989 | Davis et al. |
| 4,900,414 | A | 2/1990 | Sibalis |
| 4,936,962 | A | 6/1990 | Hatzidimitriu |
| 5,045,204 | A | 9/1991 | Dasgupta et al. |
| 5,078,853 | A | 1/1992 | Manning et al. |

(Continued)

FOREIGN PATENT DOCUMENTS

| | | |
|---|---|---|
| CN | 102079781 A | 6/2011 |
| EP | 0 979 868 A2 | 2/2000 |

(Continued)

OTHER PUBLICATIONS

Lu et al., "A Microfabricated Device for Subcellular Organelle Sorting," Anal. Chem. 2004, 76, 5705-5712.*

(Continued)

*Primary Examiner* — Alexander Noguerola
(74) *Attorney, Agent, or Firm* — Kilpatrick Townsend & Stockton LLP

(57) ABSTRACT

Methods and devices for purification of different cell components from the same sample are provided.

19 Claims, 14 Drawing Sheets

(56) References Cited

U.S. PATENT DOCUMENTS

| | | | |
|---|---|---|---|
| 5,082,548 | A | 1/1992 | Faupel et al. |
| 5,160,594 | A | 11/1992 | Huff et al. |
| 5,198,086 | A | 3/1993 | Chlanda et al. |
| 5,437,774 | A | 8/1995 | Laustsen |
| 5,567,293 | A | 10/1996 | Paleologou et al. |
| 5,646,001 | A | 7/1997 | Terstappen et al. |
| 5,650,055 | A | 7/1997 | Margolis |
| 5,773,645 | A | 6/1998 | Hochstrasser |
| 6,077,434 | A | 6/2000 | Srinivasan et al. |
| 6,084,091 | A | 7/2000 | Muller et al. |
| 6,129,832 | A | 10/2000 | Fuhr et al. |
| 6,225,129 | B1 | 5/2001 | Liu et al. |
| 6,660,150 | B2 | 12/2003 | Conlan et al. |
| 6,969,453 | B2 | 11/2005 | Ogle et al. |
| 6,969,614 | B1 | 11/2005 | Liotta et al. |
| 7,077,942 | B1 | 7/2006 | Conlan et al. |
| 7,390,389 | B2 | 6/2008 | Rossier et al. |
| 7,517,696 | B2 | 4/2009 | Srinivasan et al. |
| 7,615,354 | B2 | 11/2009 | Faupel et al. |
| 7,651,838 | B2 | 1/2010 | Paterlini-Brechot |
| 7,989,614 | B2 | 8/2011 | Deggerdal et al. |
| 8,293,095 | B2 * | 10/2012 | Han et al. ............... 205/787.5 |
| 2002/0043462 | A1 | 4/2002 | Ivory et al. |
| 2003/0083823 | A1 | 5/2003 | Parekh et al. |
| 2003/0168576 | A1 | 9/2003 | Panattoni |
| 2003/0205471 | A1 | 11/2003 | Speicher et al. |
| 2003/0206894 | A1 | 11/2003 | De Boer et al. |
| 2003/0226752 | A1 | 12/2003 | Vigh |
| 2004/0242849 | A1 | 12/2004 | Rylatt et al. |
| 2005/0087445 | A1 | 4/2005 | Speicher et al. |
| 2006/0029978 | A1 | 2/2006 | O'Neill et al. |
| 2006/0037860 | A1 | 2/2006 | Ogle et al. |
| 2007/0163884 | A1 | 7/2007 | Strand et al. |
| 2007/0205106 | A1 | 9/2007 | Vigh et al. |
| 2008/0035484 | A1 * | 2/2008 | Wu et al. ............... 204/548 |
| 2009/0101491 | A1 | 4/2009 | Bukshpan |
| 2009/0145777 | A1 | 6/2009 | Srinivasan |
| 2010/0155243 | A1 | 6/2010 | Schneider et al. |
| 2010/0155246 | A1 | 6/2010 | Schnelle et al. |
| 2010/0307920 | A1 | 12/2010 | Sivan et al. |
| 2011/0195527 | A1 | 8/2011 | O'Neill et al. |
| 2012/0138468 | A1 | 6/2012 | Sivan et al. |
| 2012/0145548 | A1 | 6/2012 | Sivan et al. |

FOREIGN PATENT DOCUMENTS

| | | |
|---|---|---|
| EP | 1456667 B1 | 9/2004 |
| EP | 1748340 A2 | 1/2007 |
| WO | 99/26724 A2 | 6/1999 |
| WO | 01/36449 A1 | 5/2001 |
| WO | 03/019172 A2 | 3/2003 |
| WO | 2004/083405 A2 | 9/2004 |
| WO | 2006/063625 A1 | 6/2006 |
| WO | 2007/051492 A1 | 5/2007 |
| WO | 2009/027970 A2 | 3/2009 |
| WO | 2009/133153 A1 | 11/2009 |
| WO | 2010/048173 A2 | 4/2010 |
| WO | 2010/118890 A1 | 10/2010 |
| WO | 2011/021195 A2 | 2/2011 |
| WO | 2011/021196 A2 | 2/2011 |

OTHER PUBLICATIONS

Zhan et al., Development of a simple ampholyte-free isoelectric focusing slab electrophoresis for protein fractionation, Journal of Chromatography A, 1216 (2009) 2929-2933.*

Procházková et al., "The Use of Carrier Ampholyte-Free Isoelectric Focusing for Proteomic Analysis," Chromatographia Supplement vol. 67, 2008, pp. S55-S61.*

Pospichal et al., "Micropreparative Focusing of Proteins in Carrier-Ampholyte-free Solution with Electrically Controlled Composition of Electrolytes," J. Microcolumn Separations, 7(3) 213-219 (1995).*

Munce et al., "Microfabricated System for Parallel Single-Cell Capillary Electrophoresis," Anal. Chem. 2004, 76, 4983-4989.*

International Search Report and Written Opinion from PCT/US2012/063571, dated Feb. 20, 2013 (14 pages).

International Search Report and Written Opinion from PCT/US2012/063601, dated Feb. 15, 2013 (12 pages).

International Search Report and Written Opinion from PCT/US2013/026485, dated Apr. 19, 2013 (14 pages).

International Search Report and Written Opinion from PCT/US2012/063502, dated Jan. 22, 2013 (13 pages).

U.S. Appl. No. 13/668,651, filed Nov. 5, 2012 (43 pages).

U.S. Appl. No. 13/669,023, filed Nov. 5, 2012 (69 pages).

U.S. Appl. No. 13/768,253, filed Feb. 15, 2013 (90 pages).

U.S. Appl. No. 13/803,564, filed Mar. 14, 2013 (52 pages).

"Adjusting acidity with impunity." PHYSorg.com. Dec. 22, 2009. Retrieved at physorg.com/news180726696.html (author unknown).

"Isoelectric Focusing" from *European Pharmacopoeia Edition 5.0*, Chapter 2 "Method of Analysis", Section 2.2.54 (p. 81-82). Published by the Council of Europe, Jun. 15, 2004.

"Isoelectric Focusing," *AES Application Focus* adapted from Chapter 7, Gel Electrophoresis of Proteins by David E. Garfin, pp. 197-268 in *Essential Cell Biology*, vol. 1: Cell Structure, A Practical Approach John Davey and Mike Lord, Oxford University Press, Oxford UK (2003).

Ameridia, "Bipolar Membrane Electrodialysis—Applications of Bipolar Membrane Electrodialysis"; retrieved online at ameridia.com/htm/eba.html Jul. 12, 2011.

Ameridia, "Bipolar Membrane Electrodialysis—Process Description"; retrieved online at ameridia.com/htm/ebp.html Jul. 12, 2011.

Ameridia, "Bipolar Membrane Electrodialysis—Production of Organic or Amino Acids by Bipolar Membrane Electrodialysis"; retrieved online at ameridia.com/htm/ebc.html Jul. 12, 2011.

Amersham Pharmacia Biotech, "Hoefer IsoPrime IEF Purification Unit," User Manual (47 pages), 1999.

Bazinet et al.; "Bipolar Membrane Electroacidification To Produce Bovine Milk Casein Isolate"; *J. Agric. Food Chem.*; 47:5291-5296 (1999).

Bazinet et al., "Effect of KCl and Soy Protein Concentrations on the Performance of Bipolar Membrane Electroacidification"; *J. Agric. Food Chem.*; 45:2419-2425 (1997)

Bazinet et al.; "Effect of Number of Bipolar Membranes and Temperature on the Performance of Bipolar Membrane Electroacidification"; *J. Agric. Food Chem.*; 45:3788-3794 (1997).

Biotech Daily, "Daily news on ASX-listed biotechnology companies," 4 pages, Oct. 10, 2008.

Cao, Liming (2005) *Protein Separation with Ion-exchange Membrane Chromatography*. (Master's Thesis) Retrieved online at wpi.edu/Pubs/ETD/Available/etd-050405-174109/.

Chen et al.; "Electrodialytic Membrane Suppressors for Ion Chromatography Make Programmable Buffer Generators"; *Anal. Chem.*; 84:67-75 (2012) ePub Nov. 21, 2011.

Chen et al.; "pH- and Concentration-Programmable Electrodialytic Buffer Generator"; *Anal. Chem.*; 84:59-66(2012) ePub Dec. 12, 2011.

Cheng et al.; "High-performance protein separation by ion exchange membrane partitioned free-flow isoelectric focusing system"; *Chem. Eng. Sci.*; 63:2241-2251 (2008).

Cheng et al.; "Micro-pH Control by Breaking Water and Its Applications". 15th International Conference on Miniaturized Systems for Chemistry and Life Sciences. Oct. 2-6, 2011, Seattle, Washington, USA (3 pages).

Cheng et al.; "Microscale pH Regulation by Breaking Water"; *Biomicrofluidics*; vol. 5, 046502, published online Nov. 2, 2011 (8 pages).

Cretich et al.; "Electroosmotic flow suppression in capillary electrophoresis: Chemisorption of trimethoxy silane-modified polydimethylacrylamide"; *Electrophoresis*; 26:1913-1919 (2005).

Das et al.; "Effects of separation length and voltage on isoelectric focusing in a plastic microfluidic device"; *Electrophoresis*; 27:3619-3626 (2006).

Denver Instrument, "Titration—Coulometric Karl Fischer Titration" brochure. (n.d.).

Dionex Corporation, "Eluent Suppressors for Ion Chromatography," Data Sheet (24 pages), 2010.

(56) References Cited

OTHER PUBLICATIONS

DKK-TOA Corporation, "AUT-701 Automatic Titrator" brochure. Jan. 10, 2008.
Douglas Instruments, "Oryx8" brochure. (n.d.).
Gregor, H.; "Ion-Exchange Membranes—Correlation Between Structure and Function"; *Pure Appl. Chem.*; 16(2-3)329-350 (1968).
Horvath et al.; "Multifunctional apparatus for electrokinetic processing of proteins"; *Electrophoresis*; 15:968-971 (1994).
Huang et al.; "Application of electrodialysis to the production of organic acids: State-of-the-art and recent developments"; *J. Membr. Sci.*; 288:1-12 (2007) ePub Nov. 25, 2006.
Huang et al.; "Capillary Isoelectric Focusing without Carrier Ampholytes"*Anal. Chem.*; 72:4758-4761 (2000).
Huang et al.; "Digitally Controlled Electrophoretic Focusing"; *Anal. Chem.*; 71(8):1628-1632 (1999) ePub Mar. 9, 1999.
Huang et al.; "The transitional isoelectric focusing process"; *Anal. Bioanal. Chem.*; 382:783-788 (2005).
Ivory, C.F.; "A Brief Review of Alternative Electrofocusing Techniques"; *Separation Science and Technology*; 35(11):1777-1793 (2000).
Jong et al., "Membranes and microfluidics: a review"; *Lab Chip*; (6):1125-1139 (2006).
Karaltay Scientific Instruments, "Laboratory electrochemical analytical instruments—Automatic potentiometric titrators." 5 pages. (n.d.).
Karimi et al.; "Electroosmotic flow through polymer electrolyte membranes in PEM fuel cells"; *Journal of Power Sources*; 140:1-11 (2005).
Kelly et al.; "Electric field gradient focusing"; *J. Sep. Sci.*; 28:1985-1993 (2005).
Kohlmann, F.J.; "What is pH and how is it measured?—A Technical Handbook for Industry"; Lit. No. G004. 24 pages. Hach Company (2003).
Lee et al.; "Polymer Electrolyte Membranes for Fuel Cells"; *J. Ind. Eng. Chem.*; 12(2):175-183 (2006).
Li et al.; "An electrokinetic bioreactor: using direct electric current for enhanced lactic acid fermentation and product recovery"; *Tetrahedron*; 60:655-661 (2004).
Lutin et al.; "Keep it natural ? Adjusting the pH of food products without chemical additives thanks to Bipolar Membrane Electrodialysis." Presented on May 15, 2007. NAMS 2007 Annual Meeting May 11-16, 2007, Orlando, Florida (3 pages).
Ly, Linda. (2008). *Development of Selective Electrophoresis for Proteins and Peptides within Proteomes.* (Doctoral Dissertation) Retrieved from web at http://www.unsworks.unsw.edu.au/primo_library/libweb/action/dlDisplay.do?vid=UNSWORKS&docId=unsworks_4279.
Mettler Toledo, "Compact Titrator G20" brochure. Sep. 2009.
Michél et al.; "Protein fractionation in a multicompartment device using Off-Gel™ isolectric focusing"; *Electrophoresis*; 24:3-11 (2003).
Montgomery et al.; "Dynamic Isoelectric Focusing for Proteomics"; *Anal. Chem.*; 78:6511-6518 (2006).
Nagasubramanian et al.; "Use of Bipolar Membranes for Generation of Acid and Base—An Engineering and Economic Analysis"; *J. Membr. Sci.*; 2:109-124 (1977).
Nguyen et al.; "A Water and Heat Management Modle for Proton-Exchange-Membrane Fuel Cells"; J. Electrochem. Soc.; *J. Electrochem. Soc.*, 140(8):2178-2186 (Aug. 1993).
NuSep Press Release, "NuSep Increases Profit Forecast to $1m after it Acquires BioInquire and completes Placement at 30c"; 2009 (4 pages).
NuSep Press Release, "NuSep Investor Presentations"; 2009 (4 pages).
NuSep, "Desalting protein samples by electro-dialysis using the ProteomeSep MF10," Application Note NAN004 (2 pages), n.d.
NuSep, "ProteomeSep—MF10 Membrane Fractionation Instrument for protein separations," Operators Manual (22 pages), 2008.
NuSep, "Removal of urea from protein samples using the ProteomeSep MF10," Application Note NAN005 (2 pages), n.d.
NuSep, "Separation of protein based on isoelectric point using the NuSep MF10," Application Note NAN001, Insert PII-055v1.1 (2 pages), n.d.
NuSep, MF10 Brochure (8 pages), (2008).
Ogle et al.; "Preparative-scale isoelectric trapping separations using a modified Gradiflow unit"; *J. Chromatogr. A*; 979:155-161 (2002).
PC Cell GmbH, "PCCell EE 64 0 04" brochure. (n.d.).
Pearson et al.; "Production of synthetic ampholytes for isolectric focusing." (1979). *Nebraska Game and Parks Commission—White Papers, Conference Presentations, & Manuscripts.* Paper 13. Retrived onling at digitalcommons.unl.edu/nebgamewhitepap/13.
Piruska et al.; "The autofluorescence of plastic materials and chips measured under laser irradiation"; *Lab Chip*; 5:1348-1354 (2005) ePub Nov. 1, 2005.
Pospíchal et al.; "Analytical aspects of carrier ampholyte-free isoelectric focusing"; *J. Chromatog. A*; 918:195-203 (2001).
Pospíchal et al.; "Electrically controlled electrofocusing of ampholytes between two zones of modified electrolyte with two different values of pH"; *J. Chromatog.*; 638:179-186 (1993).
Pospíchal et al.; "Micropreparative Focusing of Proteins in Carrier-Ampholyte-free Solution with Electrically Controlled Compositions of Electrolytes"; *J. Microcolumn Separations*; 7(3):213-219 (1995).
Ramierz et al.; "Current-voltage curves of bipolar membranes"; *J. Appl. Phys.*, 72(1):259-264 (Jul. 1992).
Silvertand et al.; "Recent developments in capillary isoelectric focusing"; *J. Chromatog. A*; 1204:157-170 (2008).
Silvertand, Linda H.H. (2009) *Isoelectric Focusing: Sample Pretreatment—Separation—Hyphenation.* (Doctoral Dissertation) Retreived online at igitur-archive.library.uu.nl/dissertations/2010-0106-200200/UUindex.html.
Song et al.; "Fabrication and Characterization of Photpatterned Polymer Membranes for Protein Concentration and Dialysis in Microchips" in Hilton Head, South Carolina MEMS Workshop Jun. 6-10, 2004 (May 2004).
Standard Operating Procedure, "SOP for Gradiflow MF10 (prototype)," 6 pages, (2007).
TechniKrom, "New cGMP Bioprocessing Tool: Automated Rapid pH Adjustment Systems" brochure. (2006).
Thomas et al.; "Gradipore™—The Preparative Electrophoresis System, Gradiflow™"; Poster MB-04, 1 page, n.d.
Thomas et al.; "Preparative electrophoresis: a general method for the purification of polyclonal antibodies"; *J. Chromatogr. A*; 944:161-168 (2002).
Thomas et al.; Gradipore, "Comparison of Gradiflow and Affinity Chromatography Methods of Antibody Preparation," Gradipore Application Note AN3004 (Jul. 2003).
Thormann et al.; "High-resolution computer simulation of the dynamics of isoelectric focusing using carrier ampholytes: Focusing with concurrent electrophoretic mobilization is an isotachophoretic process"; *Electrophoresis*; 27:968-983 (2006).
Tongwen et al.; "Citric acid production by electrodialysis with bipolar membranes"; *Chemical Engineering and Processing*; 41:519-524 (2002).
Walter et al.; "Protein microarrays: Reduced autofluorescence and improved LOD"; *Eng. Life Sci.*; 10(2):103-108 (2010).
Wei et al.; "One-step concentration of analytes based on dynamic change in pH in capillary zone electrophoresis"; *Anal. Chem.*; 74:934-940 (2002).
Wei et al.; "On-line concentration of proteins and peptides in capillary zone electrophoresis with an etched porous joint"; *Anal. Chem.*; 74:3899-3905 (2002).
Wellhausen et al.; "Facing Current Quantification Challenges in ProteinMicroarrays"; *J. Biomed. Biotechnol.*; vol. 2012, Article ID 831347, 8 pages, ePub Apr. 24, 2012.
Westermeier et al.; "Protein Detection Methods in Proteomics Research"; *Bioscience Reports*; 25(1/2):19-32 (2005).
Wilhelm, Friedrich G. (2001) Bipolar Membrane Electrodialysis. (Doctoral Thesis) Retrieved online at tup.utwente.nl/uk/catalogue/technical/electrodialysis.
Wong et al.; "Application of bipolar electrodialysis to *E. coli* fermentation for simultaneous acetate removal and pH control"; Biotechnol. Lett.; 32:1053-1057 (2010) ePub Apr. 11, 2010.

(56) References Cited

OTHER PUBLICATIONS

Wong, Michael. (2011) *Application of electrodialysis in integrated microbial fermentation and enzymatic biotransformation processes*. (Doctoral Thesis) Retreived online at discovery.ucl.ac.uk/1310480/1/1310480. pdf.

Wu et al.; "Isoelectric focusing sample injection for capillary electrophoresis of proteins"; *Electrophoresis*; 26:563-570 (2005).

Xu et al.; "Development of bipolar membrane-based processes"; *Desalination*; 140:247-258 (2001).

Xu et al.; "Electrodialysis-Based Separation Technologies: A Critical Review"; *American Institute of Chemical Engineers Journal*; 54(12):3147-3159 (2008) ePub Oct. 2, 2008.

Xu et al.; "Ion exchange membranes: State of their development and perspective"; *J. Membr. Sci.*; 263:1-29 (2005).

Zhang et al.; "Isoelectric Focusing Sample Injection for Capillary Zone Electrophoresis in a Fused Silica Capillary"; *Analytical Sciences*; 22:1039-1041 (Jul. 2006).

Zuo et al.; "A Method for Global Analysis of Complex Proteomes Using Sample Prefractionation by Solution Isoelectrofocusing Prior to Two-Dimensional Electrophoresis"; *Anal. Biochem.*; 284:266-278 (2000).

Non-Final OA mailed on Sep. 10, 2013 for U.S. Appl. No. 13/669,023, filed Nov. 5, 2012.

Final OA mailed Mar. 26, 2014 for U.S. Appl. No. 13/669,023, filed Nov. 5, 2012.

International Search Report and Written Opinion from PCT/US2013/032906, dated Jun. 14, 2013 (9 pages).

U.S. Appl. No. 14/468,730, filed Aug. 26, 2014 (108 pages).

Supplementary European Search Report dated Apr. 15, 2015 for EP Application No. 12845192.9, 6 pages.

Hughes et al., "Microfluidic integration for automated targeted proteomic assays", *Proceeding of the National Academy of Sciences*, 109(16):5972-5977 (2012).

Knittle et al., "Laser-induced flurescence detector for capillary-based isoelectric immunoblot assay", *Analytical Chemistry*, 79(24): 9478-9483 (2007).

O'Neill et al., "Isoelectric focusing technology quantifies protein signaling in 25 cells", *Proceedings of the National Academy of Sciences, National Academy of Sciences*, 103(44): 16153-16158 (2006).

Shimura et al., "Affinity Probe Capillary Electrophoresis: Analysis of Recombinant Human Growth Hormone with a Fluorescent Labeled Antibody Fragment", *Analytical Chemistry*, 66(1): 9-15 (1994).

The Extended European Searach Report dated Jun. 22, 2015 for European Patent Application No. 12844702.6, 7 pages.

Non-Final Office Action dated Aug. 5, 2015 for U.S. Appl. No. 13/803,564, 24 pages.

Armstrong et al., "Separating Microbes in the Manner of Molecules. 1. Capillary Electrokinetic Approaches", *Anal. Chem*, 71: 5465-5469 (1999).

Cabrera et al., "Continous concentration of bacteria in a microfluidic flow cell using electrokinetic techniques", *Eletrophoresis*, 22:355-362 (2001).

The Extended European Search Report dated Sep. 18, 2015 for European Patent Application No. 12845686.0, 11 pages.

* cited by examiner

SIMULTANEOUS PURIFICATION OF CELL COMPONENTS

CROSS-REFERENCE TO RELATED PATENT APPLICATIONS

The present application claims benefit of priority to U.S. Provisional Patent Application Nos. 61/555,689 and 61/555,708, both filed on Nov. 4, 2011, and each incorporated by reference.

BACKGROUND

Current isoelectric focusing based protein, peptide, nucleic acid, organelle and cell fractionation technologies suffer from two main shortcomings. First, samples are separated over a fixed or limited pH range resulting in non-optimal fractionation of various samples. Second, pH gradients required for sample fractionation are established via chemicals (ampholytes) resulting in contamination of fractionated samples with chemicals and (potential) interference of downstream analysis.

BRIEF DESCRIPTION OF THE DRAWINGS

FIG. 11A shows time=0. FIG. 11B shows time=15 minutes, i.e., 15 minutes after current was applied, resulting in separation of DNA and peptide.

BRIEF SUMMARY OF THE INVENTION

Figure 1A:
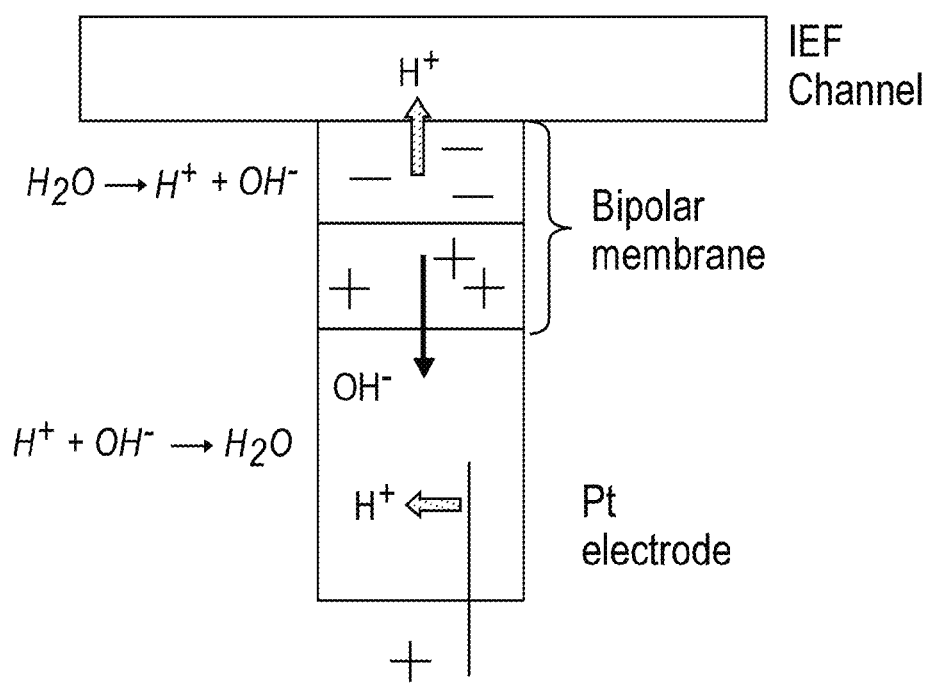
FIGS. 1A and 1B illustrate a proton and hydroxide injector, respectively, comprising a small compartment adjacent to the channel, with a Pt electrode dipped inside it, and a bipolar membrane separating the compartment from the channel.

In some embodiments, a method of purifying at least one cellular component from a biological sample is provided. In some embodiments, the sample comprises one or more cells. In some embodiments, the method comprises providing into a chamber the sample comprising a cell lysate from the one or more cells; and generating a pH gradient or pH step in the chamber with one or more proton injector(s) and/or hydroxide injector(s), such that at least two components from the cells in different positions are positioned in the chamber based on the isoelectric point (pI) of the components, thereby purifying at least one cellular component from a different cellular component.

In some embodiments, the method comprises detecting the presence or quantity of at least one of the at least two components.

In some embodiments, the method comprises collecting the at least one of the at least two different components, thereby purifying at least component from the same biological sample.

In some embodiments, the method comprises separately collecting two different cellular components from the same biological sample, thereby purifying the two components from the same biological sample.

In some embodiments, the components are moved through the inside of the chamber in one path and at least some of the components are separately collected from an orifice in the chamber. In some embodiments, the components are moved down the inside of the chamber in one path and the components are separately collected from orifices in the chamber perpendicular to the path of the components. In some embodiments, the orifices (e.g., slits or other openings) are positioned in the chamber to correspond to the pI of the components.

In some embodiments, the components are moved electrophoretically. In some embodiments, the components are moved by pumping fluid in the chamber.

In some embodiments, the at least two components are positioned electrophoretically in the chamber.

In some embodiments, one or more cells are lysed and subsequently provided into the chamber to generate the cell lysate.

In some embodiments, wherein one or more cells are lysed in the chamber. In some embodiments, the cells are lysed by generation of a pH sufficiently high or low to lyse the one or more cells.

In some embodiments, the at least one or two components are selected from nuclei, DNA, RNA, peptide, and protein.

In some embodiments, the different components are different subcellular compartments and/or organelles.

In some embodiments, the lysate is from a single cell.

In some embodiments, an agent having affinity for a target cellular component is linked to a position in the chamber and components of the cell lysate are moved to or passed the agent, thereby binding the target cellular component to the agent. In some embodiments, the target cellular component is RNA and the agent comprises an oligonucleotide. In some embodiments, the oligonucleotide comprises a poly-T sequence sufficient to bind poly adenylated RNA.

Also provided is a device or system for capturing a cell, cellular component, or virus from a biological sample. In some embodiments, the device or system comprises: a chamber for containing a solution having a biological sample along an axis, wherein the chamber comprises one or more slit or other opening in the surface of the chamber in communication with one or more proton injector(s) or hydroxide injector(s), and wherein the chamber comprises an agent linked to a position in the chamber, wherein the agent has affinity for a target cellular component, cell, or virus; an electrical source for applying an electric field in the injector(s) and optionally along the axis in the chamber; the one or more proton injector(s) or hydroxide injector(s) for establishing a pH gradient along said axis in said chamber by injecting ion flows, capable of forming one or more pH steps in a pH gradient; and a controller which operates said one or more ion sources to adjust the pH gradient so as to induce positioning of charged components, cells or viruses along the axis in the chamber. In some embodiments, the agent comprises an oligonucleotide. In some embodiments, the oligonucleotide comprises a poly-T sequence sufficient to bind poly adenylated RNA.

Also provided is a method for separating one or more target cell type or virus from at least one other cell type in a mixture and/or concentrating a target cell type or virus from a mixture. In some embodiments, the method comprises providing into a chamber the mixture and buffered solution; and generating a pH gradient or pH step in the chamber with one or more proton and/or hydroxide injector, thereby positioning cells in the chamber based on the isoelectric point (pI) of the cells or viruses.

In some embodiments, the method further comprises detecting the presence or quantity of cells or viruses at one position in the chamber.

In some embodiments, the method further comprises collecting one or more cell or virus based on the one or more cell's or virus' pI.

In some embodiments, the method further comprises separately collecting one or more cell or virus based on two or more separate pI of different cells or viruses.

In some embodiments, the cells or viruses are moved down the inside of the chamber in one path and at least some of the cells or viruses are separately collected from an orifice in the chamber. In some embodiments, wherein the cells or viruses are moved down the inside of the chamber in one path and the cells or viruses are separately collected from orifices in the chamber perpendicular to the path of the cells or viruses. In some embodiments, the orifices are positioned in the chamber to correspond to the pI of the cells or viruses.

In some embodiments, the cells or viruses are moved from the chamber electrophoretically. In some embodiments, the cells or viruses are moved from the chamber by pumping fluid in the chamber.

In some embodiments, the cells or viruses are positioned within the chamber electrophoretically.

In some embodiments, the method further comprises detecting one or more target cell type or virus positioned in the chamber.

In some embodiments, the method further comprises isolating one or more target cell type or virus from the chamber, thereby separating the target cell type or virus from at least one other cell type in the mixture.

In some embodiments, the method comprises concentrating a cell type or virus from the mixture.

In some embodiments, the cell type is a bacterium.

In some embodiments, the pH step or pH gradient separates a virus from at least one cell in the mixture.

In some embodiments, the target cell is a eukaryotic cell or a prokaryotic cell. In some embodiments, the target cell is a tumor cell. In some embodiments, the target cell is a B-lymphocyte cell or a T-lymphocyte cell. In some embodiments, the mixture is a biological sample from a human.

In some embodiments, the sample is a blood, fecal, or urine sample. In some embodiments, the sample is a waste water sample.

In some embodiments, an agent having affinity for a target cell or virus is linked to a position in the chamber and components of the mixture are moved to or passed the agent, thereby binding the target cell or virus to the agent.

Definitions

An "affinity agent" refers to a molecule that specifically binds a target molecule. Exemplary affinity agents include, e.g., an antibody, antibody fragment, or aptamer. IN situations in which a target molecule is nucleic acid, the affinity agent can be, for example, a complementary nucleic acid.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The labels may be incorporated into, e.g., antibodies and/or other proteins at any position. Any method known in the art for conjugating the antibody to the label may be employed, e.g., using methods described in Hermanson, *Bioconjugate Techniques* 1996, Academic Press, Inc., San Diego. Alternatively, methods using high affinity interactions may achieve the same results where one of a pair of binding partners binds to the other, e.g., biotin, streptavidin. Thus, for example, an affinity agent can be directly labeled with isotopes, chromophores, lumiphores, chromogens, or indirectly labeled such as with biotin to which a streptavidin complex (optionally including, e.g., a fluorescent, radioactive, or other moiety that can be directly detected) may later bind. Thus, a biotinylated antibody is considered a "labeled antibody" as used herein.

The phrase "specifically (or selectively) binds" or "specifically (or selectively) immunoreactive with" or "having binding specificity for", when referring to an affinity agent and target molecule, refers to a binding reaction between the affinity agent and target molecule which is determinative of the presence of the target molecule in the presence of a heterogeneous population of proteins and/or other biologics. Thus, for example, under immunoassay conditions, antibodies bind to a particular protein and do not bind in a significant amount to other proteins present in the sample. Specific binding to an antibody under such conditions may require an antibody that is selected for its specificity for a particular protein. For example, antibodies raised against a protein can be selected to obtain antibodies specifically immunoreactive with that protein and not with other proteins. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See, Harlow and Lane *Antibodies, A Laboratory Manual*, Cold Spring Harbor Publications, NY (1988) for a description of immunoassay formats and conditions that can be used to determine specific immunoreactivity. Typically, a specific or selective reaction will be at least twice the background signal or noise and more typically more than 10 to 100 times background.

The term "biological sample" encompasses a variety of sample types obtained from an organism. The term encompasses bodily fluids such as blood, saliva, serum, plasma, urine and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, sedimentation, or enrichment for certain components. The term encompasses a clinical sample, and also includes cells in cell culture, cell supernatants, cell lysates, serum, plasma, other biological fluids, and tissue samples. The term is not limited to human-derived, or medical-related samples, and thus can include, e.g., plant-based, prokaryotic-based, or other samples of biological origin.

The term "antibody" refers to a polypeptide comprising a framework region (e.g., from an immunoglobulin gene), or fragments thereof, that specifically bind and recognize an antigen or desired target. Typically, the "variable region" contains the antigen-binding region of the antibody (or its functional equivalent) and controls specificity and affinity of binding. See Paul, *Fundamental Immunology* (2003).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

An "isotype" is a class of antibodies defined by the heavy chain constant region. Immunoglobulin genes include the kappa, lambda, alpha, gamma, delta, epsilon, and mu constant region genes. Light chains are classified as either kappa or lambda. Heavy chains are classified as gamma, mu, alpha, delta, or epsilon, which in turn define the isotype classes, IgG, IgM, IgA, IgD and IgE, respectively.

Antibodies can exist as intact immunoglobulins or as any of a number of well-characterized fragments that include specific antigen-binding activity. Such fragments can be produced by digestion with various peptidases. Pepsin digests an antibody below the disulfide linkages in the hinge region to produce F(ab)'$_2$, a dimer of Fab which itself is a light chain joined to $V_H$—$C_H1$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

"Target analyte" or "target molecule" can include a biomolecule, or molecule of biological origin. Target molecules include, but are not limited to, proteins, polynucleotides, metabolites, viruses, and virus-like particles and cells. Examples of proteins include but are not limited to antibodies, enzymes, growth regulators, clotting factors, and phosphoproteins. Examples of polynucleotides include DNA and RNA. Examples of viruses include enveloped and non-enveloped viruses.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide nucleic acids (PNAs).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded.

Detailed Description Of The Invention

As described in more detail herein, methods and apparatuses are provided that allow for separation of targets (e.g., cells or viruses, organelles, or other cell components) from samples in a chamber in an apparatus optionally using 1) electrical fields to move the targets combined with 2) electronic control of pH of solution in sub-areas of the chamber using proton or hydroxide injectors. The methods take advantage of the pH-dependence of charge of targets, for example allowing for localization of charged targets to a particular sub-area by setting the pH of solution in proximity to the sub-area to a pH at or close to the pI of the target of interest. In some embodiments, an electric field is applied in the chamber, and at a target's pI, the target becomes uncharged and therefore does not move further in the electric field. A number of embodiments using this aspect are described below.

Figure 2:
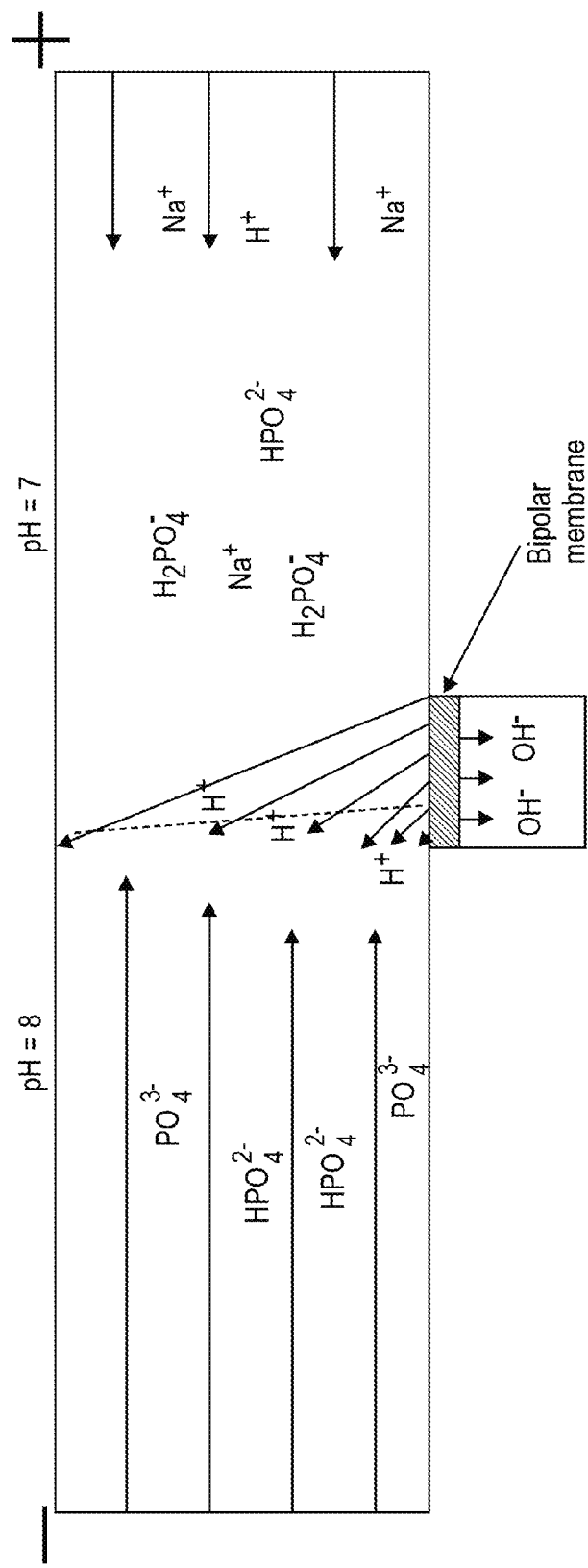
FIG. 2 illustrates possible electrolytes and their interaction with a proton injector.

The apparatus can have a variety of configurations. The chamber can comprise one or more (e.g., 1, 2, 3, 4, 5, or more) proton or hydroxide injector separated from the chamber by a bipolar membrane, wherein the injector comprises an electrode, thereby allowing for electro-hydrolysis of water molecules and localized control of pH within a region of the chamber. See, e.g., FIG. 2. In some aspects, the apparatus comprises at least one chamber having a first and second electrode, which allow for moving a charged target in an electric field.

The terms "chamber" and "channel" are used synonymously. The terms encompass containers that are considerably (e.g., 10×, 100×, 1000×) longer than wide, which allow for multiple injectors along the long axis of the chamber. Without intending to limit the scope of the invention, it is noted that chambers of the following dimensions have been constructed:

| Channel L/H/W in mm | Slit L/H/W In mm | Material | Channel volume (Vc; in µl) | Slit volume in µl (Vs; in µl) |
|---|---|---|---|---|
| 90 × 0.3 × 3 | 3 × 0.5 × 0.3 | Glass/PMMA | 81 | 0.45 |
| 36 × 0.2 × 1 | 1 × 0.2 × 0.2 | COC | 7.2 | 0.04 |
| 221 × 0.25 × 1 | 1 × 0.25 × 0.2 | PMMA | 55 | 0.05 |
| 36 × 0.15 × .5 | .5 × 0.1 × 0.1 | PMMA | 2.7 | 0.005 |
| 33.6 × 0.25 × 1 | 1 × 0.25 × 0.23 | PMMA | 8.4 | 0.0575 |
| 221 × 0.25 × 1 | 1 × 0.25 × 0.2 | PMMA | 55 | 0.05 |

"Slits" refer to the size of the hole in the chamber through which the proton or hydroxide injector is connected to the chamber. A bipolar membrane at the slit divides the chamber from the injector.

The chamber/channel can also comprise one or more opening (e.g., orifice or port), optionally controlled by a valve, for collection.

The orientation of the electrodes (i.e., which is a cathode and which an anode) will depend on the charge of the molecules to be moved in the solution and the direction the molecules are to be moved. For example, a positively-charged molecule moves towards a cathode and a negatively-charged molecule moves towards an anode when an electrical voltage difference is present through the solution in the chamber between the cathode to the anode.

Generally, the electrodes should be oriented so that they are as close to each other as possible, i.e., directly across from each other. While other configurations are contemplated and possible, voltage and resistance increases as a function of distance.

Electrodes in the chamber can in some circumstances interfere and/or bind target molecules (e.g., protein) in the chamber. Thus, in some embodiments, the electrodes are separated from the chamber by a membrane or gel, thereby preventing target molecules from binding the electrodes.

Figure 4:
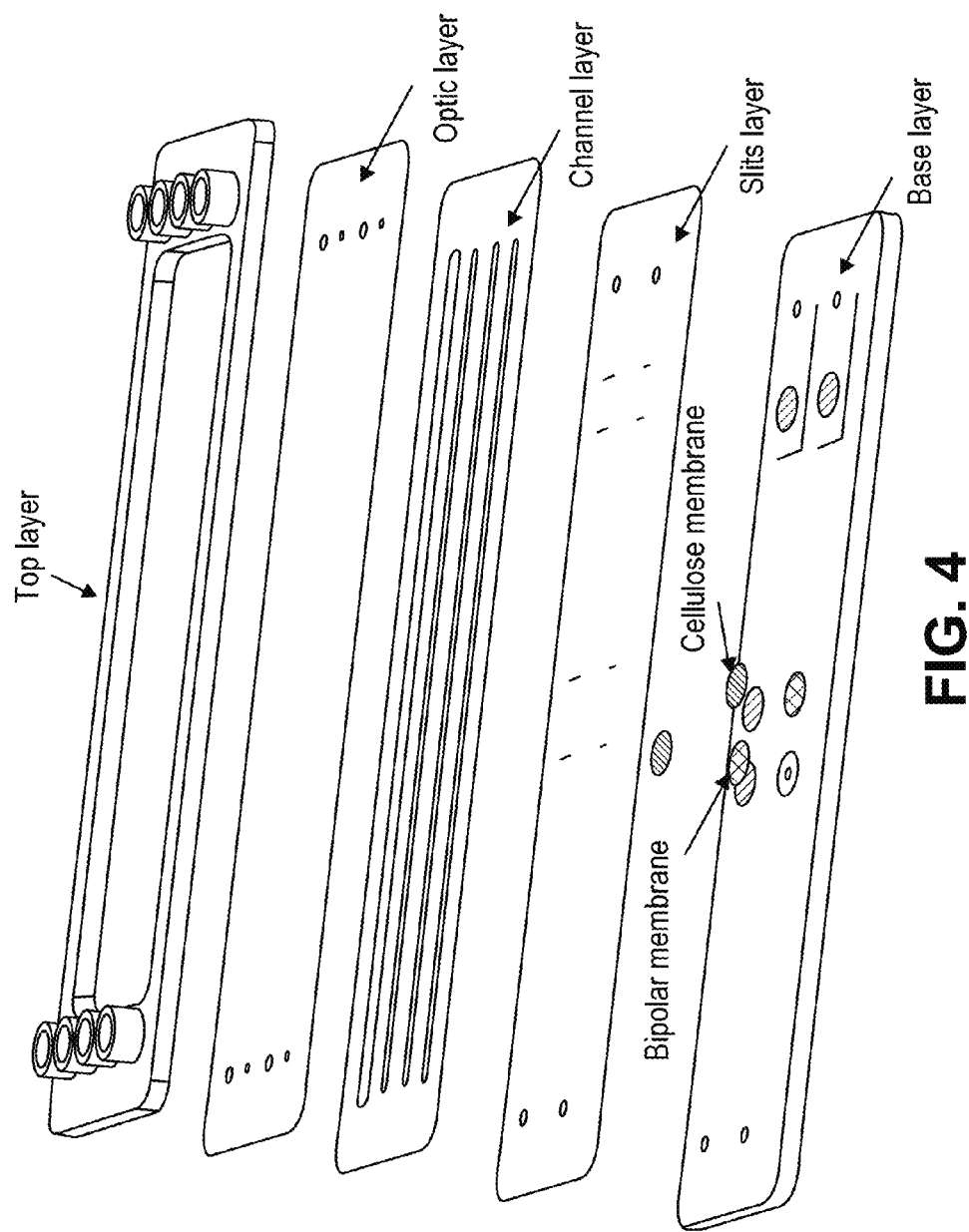
FIG. 4 illustrates an embodiment of an integrated disposable channel for use in a proton/hydroxide injector device. Slits for fluid contact to proton/hydroxide injector compartments can be arranged as desired. For example, in some embodiments, slits in the chamber are 1-1000 microns, and in some embodiments, about 100 micron. The number and size of slits can be designed to generate step-wise pH gradients as desired. Cellulose, or other hydrophilic, membranes, for example, as shown in FIG. 4 are optional, and function to cover unused slits and/or can optionally cover bipolar membranes to the extent sample components have affinity to the bipolar membrane. In some embodiments, instead of hydrophilic membranes, hydrophilic coatings may be used to cover the bipolar membranes and prevent binding of the sample components to it. Further slits can be used to extract from, and inject samples to, the channel.

The size and shape of the chamber can vary. While the chamber is depicted as a tube or channel (i.e., longer between the electrodes than across other axis), other configurations are also possible. In some embodiments, the channel can be constructed as illustrated in FIG. 4.

An ion "injector" refers to one or more compartments, separated from a sub-chamber or other vessel (e.g., such as a reservoir), by a hole or "slit" and divided by a bipolar membrane(s), wherein the compartment(s) contain an electrode(s). Depending on the orientation of the electric field (e.g., orientation of the anode and cathode) in the compartment(s), the compartment(s) can be designed to inject protons or hydroxide ions through the selective membrane(s) and into the adjacent chamber.

By controlling the current and configuration, one can thereby control the pH of solution in the chamber in proximity to the proton or hydroxide injector. Generally, it can be desirable to increase the surface area of the bipolar membrane as this allows for decreased electrical resistance.

The membrane(s) "divides" the compartments from the chamber by forming a barrier that separates solution in a compartment from the chamber, e.g., at least to the level of solution in the chamber. For example, in embodiments in which the chamber is open at the top (or alternatively, has a top cover that can be removed), the membrane(s) can be designed to completely divide a compartment from the chamber at least up to the level of solution in the chamber and/or compartment, or to a level designated as a maximum for solution loading. As desired, the membranes can be designed to be higher than the solution level so as to avoid accidental transfer (e.g., splashing) from one portion to another. If desired, the membranes can be "framed" by a solid material (e.g., plastic) or otherwise anchored between the chamber and the compartment.

The electrodes can be formed from any conducting or semi-conducting substance. For example, in some embodiments, one or more electrode comprises a metal. In some embodiments, the metal is zinc, copper, or platinum. For example, the electrodes can be platinum or can be platinum-plated. Generally, maximal surface area for electrodes is desirable. A flattened electrode, for example, provides more surface area than a wire.

International Patent Application Publication No. WO2009/027970 describes methods and devices (i.e., proton or hydroxide injectors) useful in producing local concentrations of protons or hydroxide ions, proton or hydroxide concentration gradients, and desired proton or hydroxide concentration topographies in an environment, such as an electrolyte solution, a gel, and the like. International Patent Application Publication No. WO2011/021195 and WO2011/021196 describe methods and devices for isoelectric focusing proton/hydroxide injectors and also describes display of data.

Figure 1B:
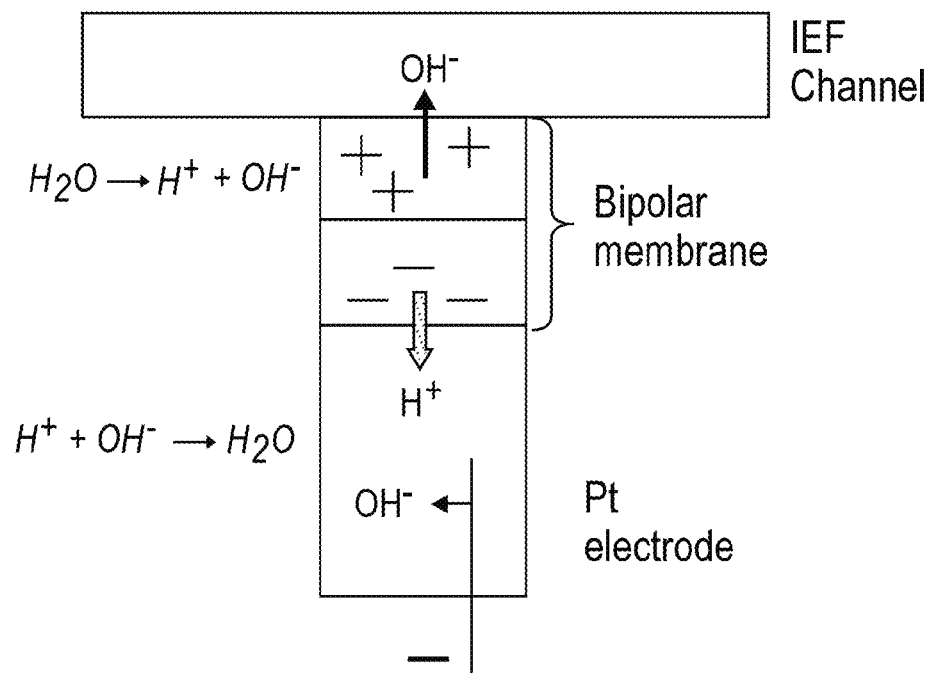

Proton/hydroxide injector technology can be used to affect the pH of the solution in a chamber, or at least the solution in the chamber in proximity to the injector. Briefly, in some embodiments, the proton/hydroxide injector comprises a compartment adjacent to the apparatus chamber, with an electrode inside the compartment, and a bipolar membrane separating the compartment from the channel. See, e.g., FIGS. 1A-1B. A bipolar membrane is an ion-exchange membrane having a structure in which a cation-exchange membrane and an anion-exchange membrane are joined together, and allows for water molecules to be split into protons and hydroxide ions. Voltage applied between the compartment and the channel divided by the bipolar membrane leads to water splitting and injection of protons or hydroxide ions into the channel. Some advantages of this technology can include, for example, bubble-free water hydrolysis and injection of generated ions directly to the channel, allowing short response time (e.g., if desired, below 1 minute).

By applying the appropriate voltage to the electrodes in the chamber an electric field across the solution in the chamber is generated and charged molecules move accordingly. In some embodiments, the charged molecules can be added in proximity to the anode or cathode in the chamber (in which the pH is controlled at least in part by a proton injector or a hydroxide injector), and subsequently the voltage is applied, thereby delivering the charged molecule, cell, virus, organelle, etc. to a desired position in the chamber at a time determined by the user.

The direction of movement of the molecule will depend on the charge of the molecule and the polarity of the applied voltage.

Figure 3:
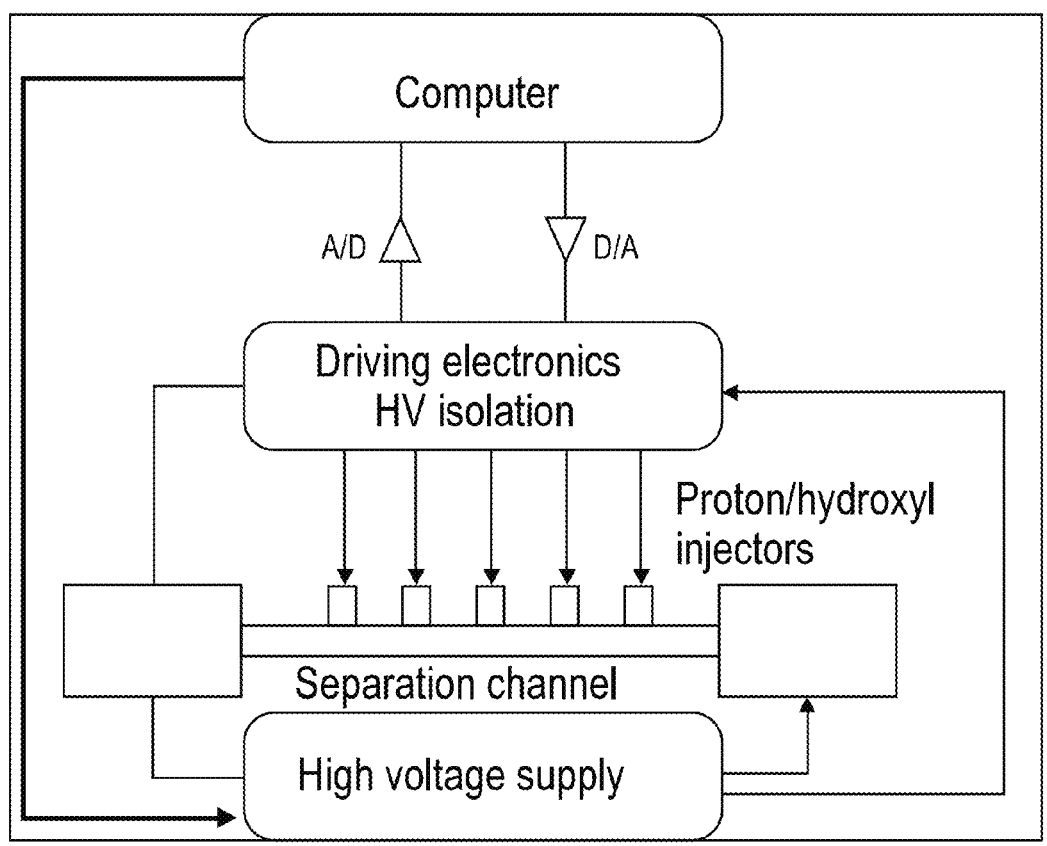
FIG. 3 illustrates an embodiment for a system controlling a proton/hydroxide injector device.

Systems incorporating the apparatus are provided. Systems can include, for example, a power supply and power regulator to control current and/or voltage to electrodes in the chamber and/or injectors. See, e.g., FIG. 3. Pumps for regulating flow of liquids, a mechanism for stirring or mixing solution in the chamber, and heating or cooling units can be included. In some embodiments, the system includes a pH and/or conductivity probe in the chamber. Generally, it can be desirable to place the probe at a distance from the electric field lines between electrodes to improve readings.

Figures 5A, 5B, 5C:
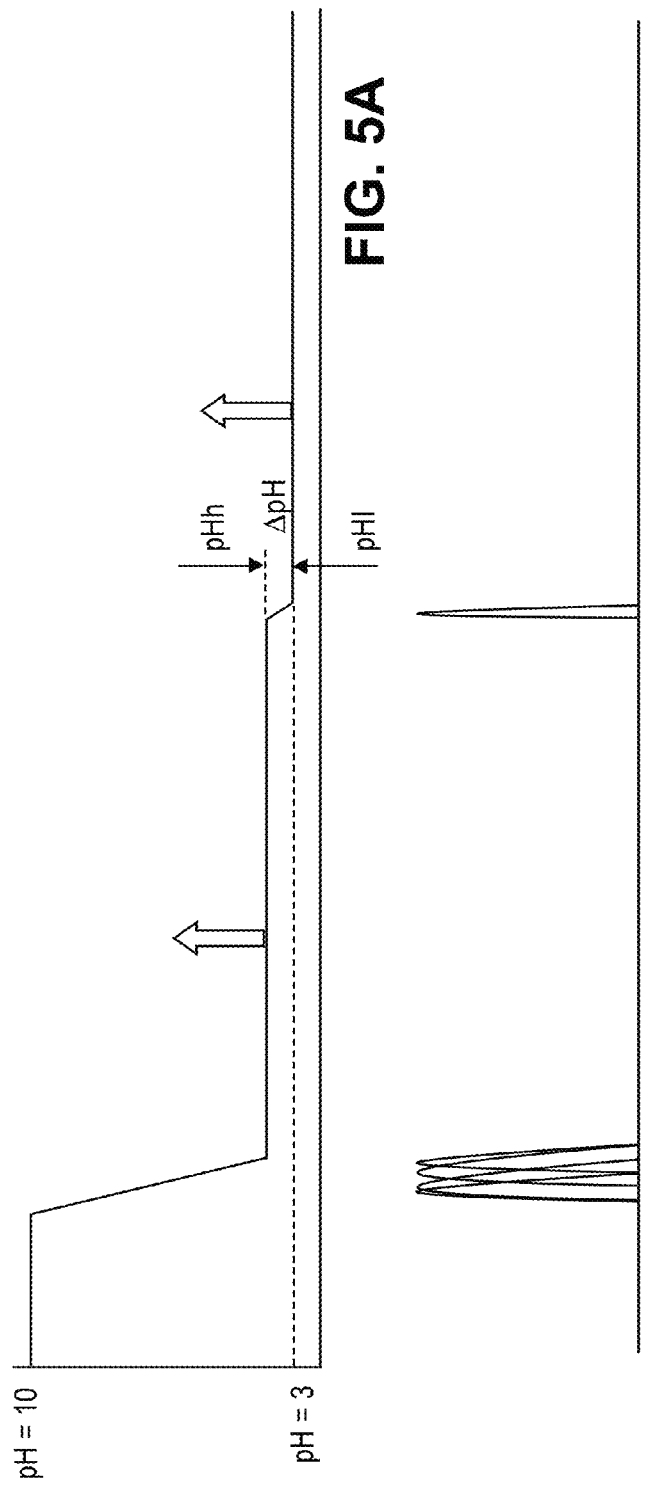
FIGS. 5A-C illustrate generation of a pH step gradient and isolation of target molecules with the gradient. In the figure, a bipolar membrane (2) generates a large pH differential, thereby focusing unwanted components (1) of the sample away from the target analyte. A second bipolar membrane (4) generates a small pH differential centered at the pI for the target analyte (3). The target analyte (3) can optionally be collected in a channel (5) in the chamber.

Dynamically adjustable pH 'step/s' spanning the pH range of ~2-12 (can be further extended or contracted as needed) can be generated within a chamber filled with suitable buffers using proton or hydroxide injectors as described herein. An example of such a gradient is displayed in FIG. 5A. Extreme pH conditions, especially basic ones, induces cell lysis by disrupting the structure of the membrane. Inducing cell lysis can be done in a highly controlled fashion by injecting OH- ions from a hydroxide injector. Subsequent cell analysis can be achieved, for example, by separating the lysate electrophoretically and/or or by affinity capture for one or more target molecules or cellular components. Using the appropriate dimensions, cell analysis can be performed with digital pH on a single cell.

In some embodiments, cellular components, e.g., complex mixtures of suitably buffered organelles or other subcellular compartments (e.g., rom lysed cells so as to maintain organelles substantially intact) or cellular components (e.g., protein, DNA, and RNA) are separated from other components, and optionally detected, quantified and/or collected and analyzed further. In some embodiments, along with separation, one or more affinity agents in the chamber (e.g., linked to a position in the chamber) are used to further capture and/or purify a target cellular component (or as described further below, an intact target cell or virus). Affinity agents can include, e.g., antibodies, aptamers, proteins, or other molecules with specific affinity for a target (e.g., biotin and avidin, complementary nucleic acids, etc.).

Figure 12:
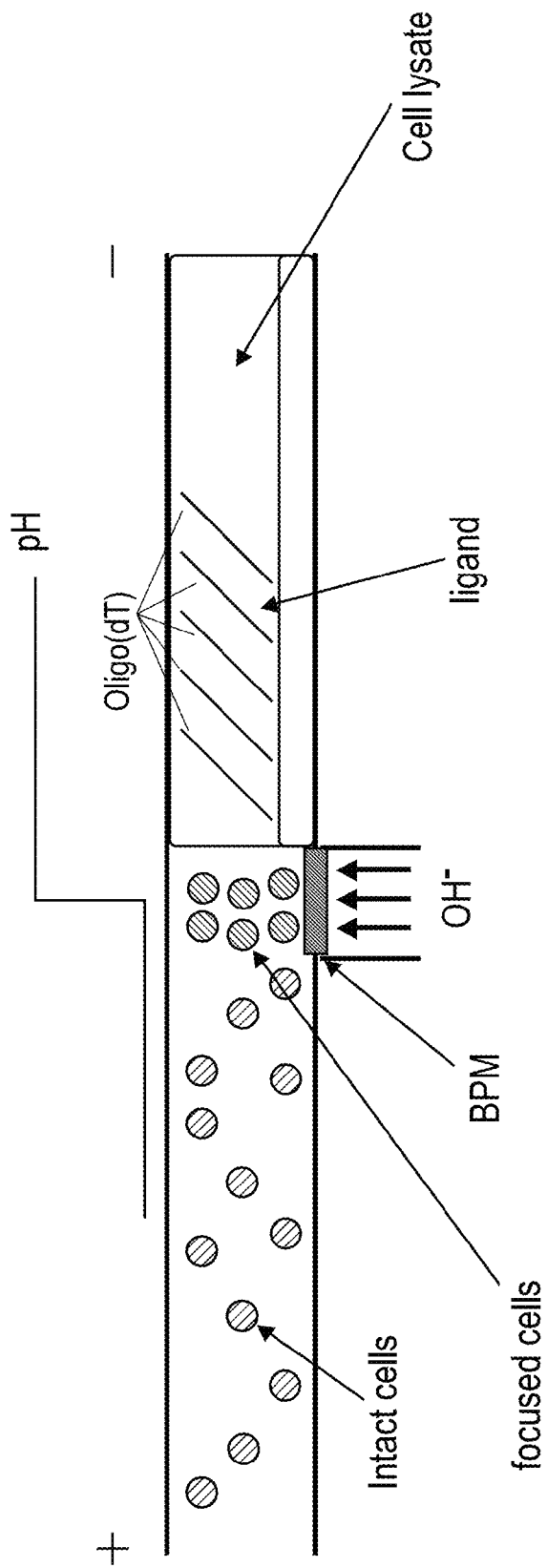
FIG. 12 presents a schematic description of a system that focuses cells, induces their lysis, and captures their mRNA using a proper ligand.

As an example, FIG. 12 presents a schematic description of a system that focuses one or more cells, induces cell lysis, and captures mRNA from the cells using a ligand. As shown in the figure, the cells migrate in a channel where a longitudinal electric field is maintained. A hydroxide injector injector is placed at one or more position along the channel creating alkaline conditions. Cells migrating (see, FIG. 12) focus on the pH step, and, due to the alkaline conditions, are lysed. In some embodiments, after the cell or cell population is lysed, the pH step is shut down. Alternatively, in some embodiments, a cell lysate or a partially purified lysate is added to the channel/chamber. The lysate subsequently leaves the region of the chamber in proximity to the hydroxide injector and continues its migration (to the right in the figure) due to the electric field generated by electrodes at either end of the channel. A ligand having specific affinity for one of the lysate components is positioned in the channel (in the figure it is an oligo-T that binds mRNA through its polyA tail, though other sequence-specific oligonucleotides are contemplated as well as other affinity agents such as antibodies, aptamers, etc., having specific affinity for the component). This ligand binds its corresponding molecule (i.e., the target cellular component) as the lysate migrates through the channel, thereby isolating the target component from other components in the sample. Release of the isolated component can be achieved, if desired by, for example, injecting an elution buffer that eliminates the affinity of the component to the ligand. In some embodiments, the elution buffer is generated with one or more proton and/or hydroxide injectors or by addition of the appropriate buffer.

In some embodiments, the lysate components can be separated by electrophoresis (not shown in the figure). In some of these embodiments, no ligand is present or used. Instead, after switching off the pH step, the whole lysate can be moved freely in the electric field generated by electrodes in the channel, and after a certain distance, will be separated from other components according to mobility. Thus, pI, mobility, or both may be used to separate components in the channel.

In some embodiments, complex mixtures of (e.g., suitably-buffered) organelles or other subcellular compartments (from lysed cells so as to maintain organelles substantially intact) or cellular components (e.g., protein, DNA, and RNA) will be electrophoresed within chamber so as to 'capture' the separate organelle or components at their respective isoelectric points in either a single pH step (see FIG. 5B) or multiple pH 'step/s' spanning the desired pH range. Subsequently, electronic adjustment of H+/OH-generation at (each) 'step' will be used to 'release' simplified mixtures of ampholyte-free, charged species towards a harvesting chamber for collection and downstream analysis. See, e.g. FIG. 5C. This approach enables optimized fractionation of various organelle or other subcellular compartments or various cellular components (DNA, RNA, protein) (via adjusting component capture and release in a sample-dependent manner) without contamination by chemical ampholytes. As described herein, this approach can also be adapted to isolate cells and/or separate cell mixtures, based on the target cells' pI.

Figure 6:
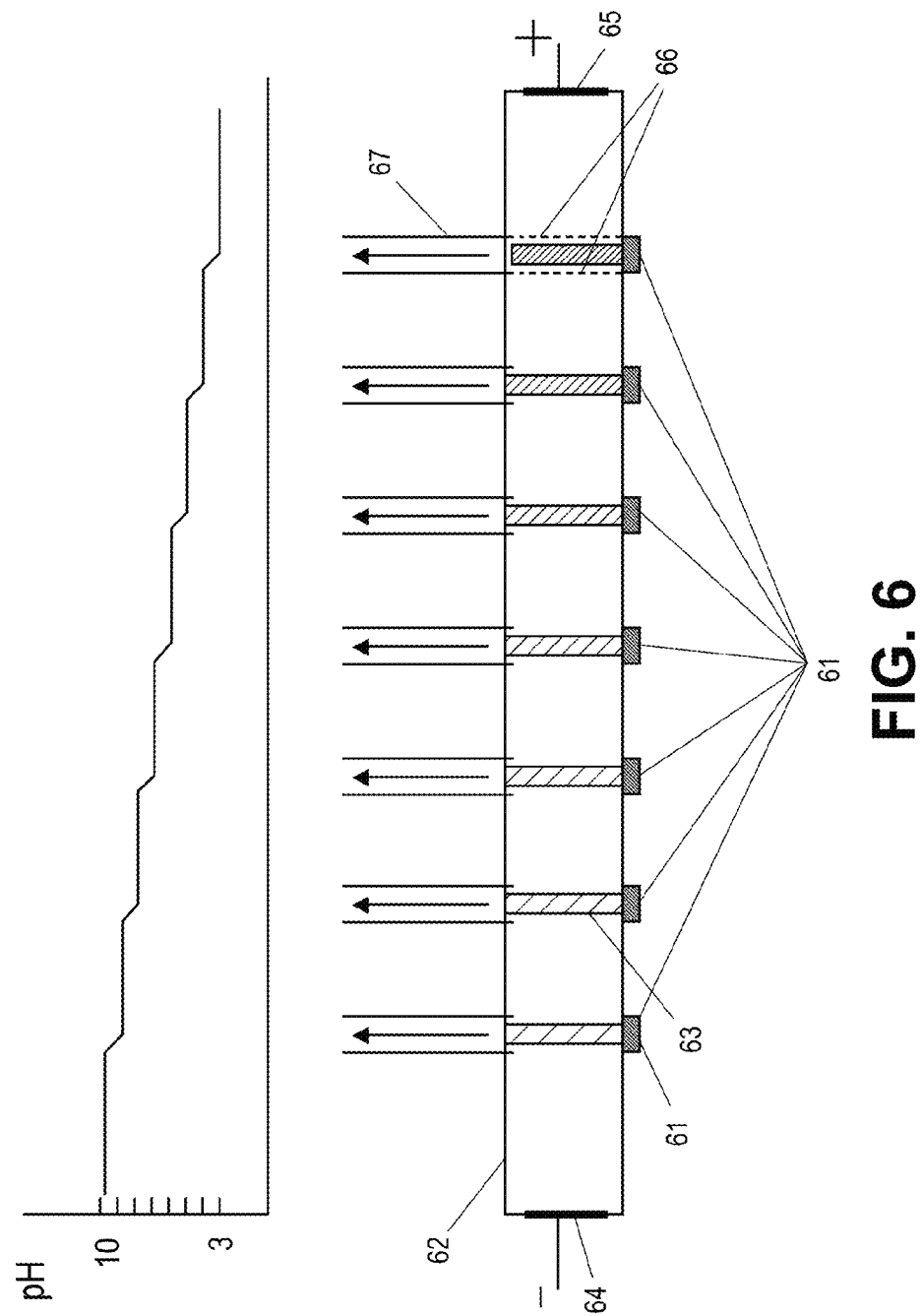
FIG. 6 illustrates generation of a pH step gradient and isolation of multiple target molecules with the gradient. This embodiment can be used for subsequent application to electrophoresis or other applications.

In some embodiments, bipolar membranes (61) are placed in slots in a channel (62) (also referred to herein as a "chamber"). See, FIG. 6. The channel can be filled with a suitable buffer. Either protons or hydroxide ions are injected by each membrane to create a step gradient is created as shown on the pH graph (FIG. 6). The cells (63) focus in the steps corresponding to their pI by applying orthogonal electric field through electrodes (64) and (65). Optional permeable membranes or screens (66) can be used to create chambers where the organelles or cellular components are focused. After the focusing is completed the organelles or cellular components are harvested through harvesting ports or channels (67).

The pI fractions can be precisely positioned where desired (for example on the top of the second dimension channel) when using a proton/hydroxide injector. With the proton/hydroxide injector systems as described herein, the target bands (target organelles or cellular components) can be delivered to the detector, thereby simplifying design.

Separation of multiple different cell components is very difficult using standard protocols. In typical isolation procedures, one cellular component is usually destroyed to isolate the others (for example, proteins and RNA are usually hydrolyzed to purify the DNA). Thus, a challenge for researchers today is isolating the DNA, RNA, and protein all from a single sample. The most convenient techniques available only enable isolation of one of the three fractions while discarding the other two.

Figure 7:
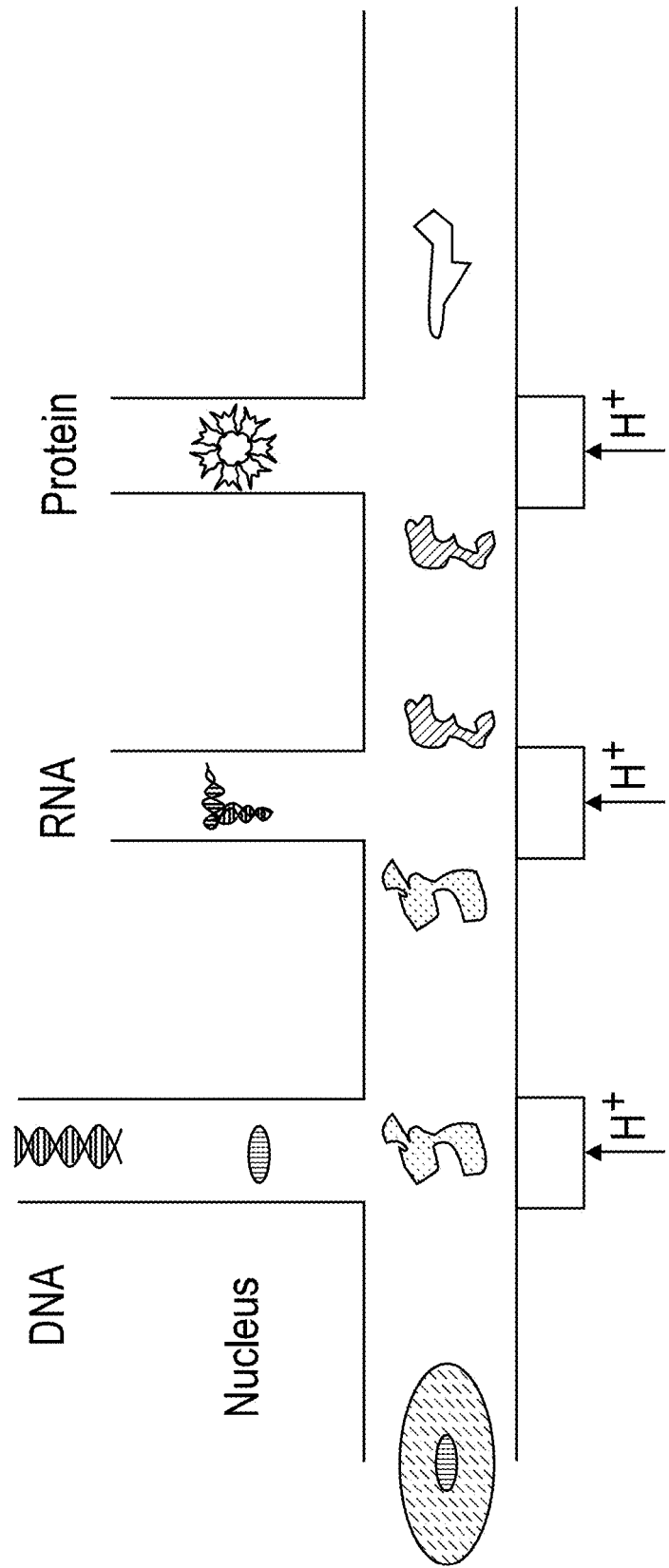
FIG. 7 illustrates an embodiment in which different cellular components (nucleic acid, proteins, etc., are purified from the same sample.

To compensate for this, the present application provides methods and devices for isolating simultaneously different components from cells without splitting a sample and simply purifying different components from different portions. The proton/hydroxide injector technology enables the isolation of all three types of biomolecules from the same sample by separating target components based on differential pI. In some embodiments, cells are moved (e.g., pumped or electrophoretically) down a channel that contains proton/hydroxide injectors at varying points along its length. See, e.g., FIG. 7. In some embodiments, at the first injector, the cells are halted and the pH is changed to lyse the cells (for example, either low pH, e.g., pH ~3 or lower or high pH, e.g., pH ~11 or higher). This will release the RNA and protein and, in some embodiments, the DNA remains inside the intact nucleus. Alternatively, a cell lysate can be provided into the channel. In some embodiments, the nucleus can be separated from the rest of the cell material by pumping or electrophoretically moving the nuclei into a side channel and subsequent DNA isolation can be performed. In some embodiments, the cellular material in the main channel can also be moved to a pump where the pH is changed (e.g., again) to separate the total RNA from the cellular material. In some embodiments, the isolated RNA will then be pumped into a side channel for collection. In some embodiments, enzymes that specifically digest DNA (DNases) or RNA (RNases) or protein (proteases) may be included in buffer-filled channel to allow for isolation of desired components and elimination of undesired components. Finally, in some embodiments, the total protein is removed from the rest of the cellular debris, e.g., by changing the pH and pumping the proteins down a collection channel. This can be performed on a single cell only for single cell analysis or on populations of cells up to at least several thousand (or more, e.g., several hundred thousand or a million).

Figure 8:
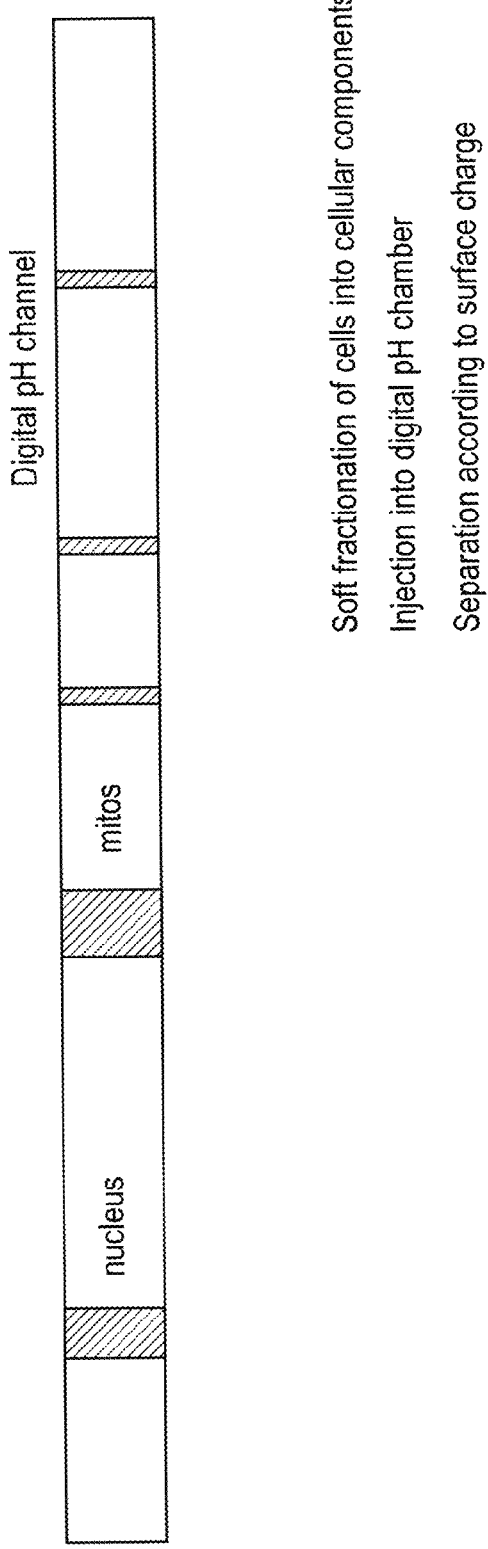
FIG. 8 illustrates an embodiment in which different subcellular compartments are separated and purified.

Alternatively, the technology can be applied to separate/isolate different cellular organelles or other subcellular compartments from each other. See, e.g., FIG. 8. Subcellular structures to be separated can include, but are not limited to, nuclei, mitochondria, lyzosome, peroxisome and the endoplasmic reticulum ER. Except for the ER, which is an integrated membrane structure and cannot easily be separated from the cell membrane with available methods, all other organelles have surface proteins and therefore surface charge or pI. If organelles precipitate at their pI, surface charge based isolation of one or more organelle of interest can be employed or appropriate buffer additives used to reduce or eliminate precipitation at pI or precipitation of non-desired organelles (or other cellular components) carried out at the pI of the non-desired organelles can be achieved, so as to maintain the organelle(s) of interest soluble for collection downstream. Organelle isolation can also be performed via proton or hydroxide ion injector technology as a second 'polishing' step starting with enriched preparations of organelle of interest. Organelles can be subsequently detected and/or quantified. Exemplary detection of quantification methods include, e.g., immunoassays and/or nucleic acid amplification or sequencing (for those organelles that contain nucleic acids).

The methods allow for isolation of organelles for study of organelle-mediated diseases. some specific diseases, associated with a particular organelles can be studies much easier. Numerous energy related processes are linked to mitochondria, for example, heart diseases and a number of age-related neural diseases, and thus the present methods could be useful for diagnostic assays for these or other diseases and conditions. In some embodiments, the cellular components may be separated based on their pI and in other embodiments, on their mobility, or using combination of both (pI and mobility).

Separation of Cell Mixtures

Standard cellular separation techniques are carried out using a range of cellular parameters including size, internal complexity, dielectric properties and or most notably presence of cell surface proteins. Much of this type of work is performed using blood samples that contain a variety of cell types. Some can be readily separated using bivariate analysis of size and internal complexity while others require immunostaining for differentiation, such as classification of B versus T lymphocytes.

Figure 9:
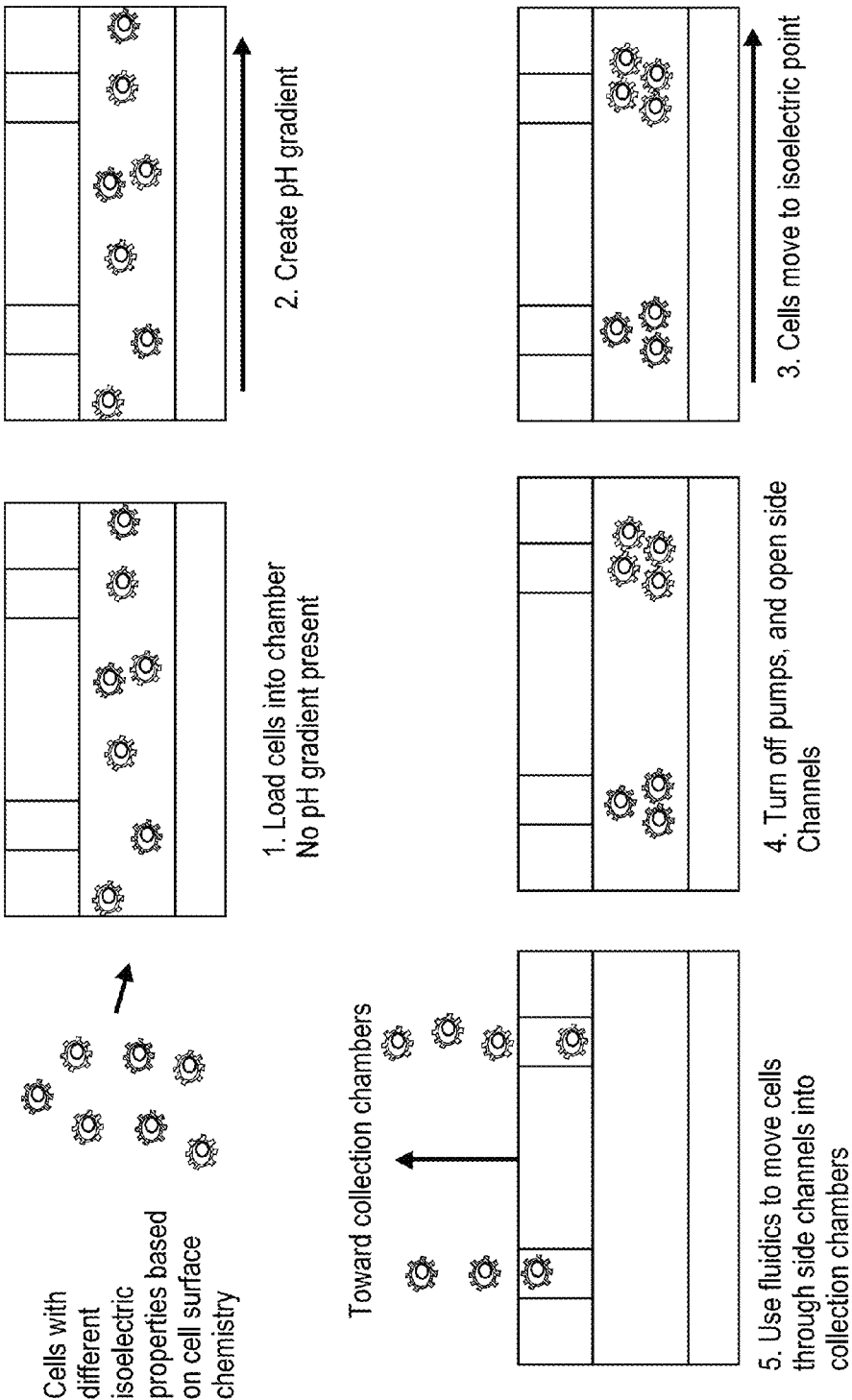
FIG. 9 illustrates an embodiment in which different cell types in a mixture are separated based on their pI and subsequently collected. While the cells are shown in the figure to be isolated via side channels in the chamber, alternatively, cells, once separated by pI, can be pumped out of an end (left or right as shown in the figure) sequentially and substantially free of the other cell type.

There are published reports of cellular separation of chicken cells, yeast and bacteria through isoelectric focusing (Vasudeva et al. (1979), *Expl. Cell Biol.* 47:360-367; Armstrong et al. (1999) *Anal. Chem.* 71:5465-5469; Shen et al. (2000) *Anal. Chem.* 72:4603-4607). The methods described here provide a new method for separating cells based on isoelectric points of the cells. A well-tuned and controllable pH gradient generated with one or more (e.g., 1, 2, 3, 4, 5, or more) proton or hydroxide injector allows for rapid and precise differentiation of cells based on their distinct isoelectric points. See, FIG. 9. In some embodiments, a mixture of at least two types of cells is loaded into the chamber, optionally without a pH gradient set by proton or hydroxide injectors in the chamber. A pH gradient is subsequently set by the injector (s), thereby focusing the at least two cell types to different positions in the chamber, based on pI. If desired, collection channels can be positioned at particular positions in the gradient, thereby allowing for collection of one or more cell type. Multiple collection channels can be designed as desired.

Exemplary cells include, e.g., prokaryotic or eukaryotic cells. This approach can be used, for example, to accurately distinguish B versus T lymphocytes prior to analysis and sorting by FACS. This approach can also be used to distinguish and allow for early detection and removal of dead or dying cells, which often confound FACS analysis. This technology allows for resolution of two of more cell types that are otherwise difficult to resolve (e.g., such as the T- and B-cells discussed above) as well as concentration of cells. Concentration of cells is of particular use in situations in which low concentrations of cells are to be detected. Examples of such embodiments include testing of waste water or food or liquids for human or animal consumption, as well as for medical testing, including but not limited to, detection and/or isolation of stem cells, tumor cells, and cancer stem cells, detection or isolation of viruses or bacteria from blood or other bodily fluids or biological samples, etc. Cells to be detected or isolated can also include, e.g., mammalian cells, plant cells, protozoa, etc.

Detection and/or quantification of the cell or virus can be achieved in a variety of ways. For example, in some embodiments, a detectably-labeled antibody or other affinity agent is contacted to the target cell or virus after the cell or virus is localized based on pI and/or is separated or collected.

All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

EXAMPLE

Example 1

Separation of Protein Components of Rotofor Standard Mix (Contains Phycocyanin, Hemoglobin and Cytochrome b).

6.55 ml Rotofor protein standard was injected at the cathode (−) end of a channel having an electrode at either end and was operated at 300 V, 14.5 mA. The channel had the following attributes:

| Channel L/H/W in mm | Slit L/H/W In mm | Material | Channel volume (Vc; in µl) | Slit volume in µl (Vs; in µl) |
|---|---|---|---|---|
| 90 × 0.3 × 3 | 3 × 0.5 × 0.3 | Glass/PMMA | 81 | 0.45 |

A first proton injector was set at 100 mA and ramped manually up to 210 mA. A second proton injector was set at 100 mA and ramped manually down to 0 mA.

Buffer used: 4 mM Sodium Citrate, 4 mM Sodium Phosphate (dibasic), 7 mM Sodium Pyrophosphate, 13 mM Sodium Sulphate, pH 10.2 (pH adjusted with NaOH)

Result:

Hemoglobin (pI ~7) was separated from Cytochrome b (pI ~9.5). Phycocyanin (pI ~4.5) was removed from mixture.

Example 2

Separation of Two Peptides with Distinct pI from One Another

Six milliliters of a 1:1 mixture of dual-labeled peptides (6.86cy5; 3 mM solution and 7.38cy3; 1 mM solution) was injected at the cathode (−) end in a channel having an electrode at either end and operated at 150V, 0.7 mA. The channel had the following attributes:

| Channel L/H/W in mm | Slit L/H/W In mm | Material | Channel volume (Vc; in μl) | Slit volume in μl (Vs; in μl) |
|---|---|---|---|---|
| .41 × 1 × 0.07 | 1 × 0.2 × 0.07 | PMMA/Teflon | 2.87 | 0.014 |

Initially, only one proton injector was operated at 60 μA (to focus the two peptides together). Subsequently, a second proton injector was ramped down and the first proton injector was ramped up at 0.5 μA per min over 30 minutes to separate the two peptides.

Buffer used: 4 mM Sodium Citrate, 4 mM Sodium Phosphate (dibasic), 4 mM Sodium Pyrophosphate, 13 mM Sodium Sulphate, pH adjusted to 8.5 (with $H_2SO_4$)

Figure 10:
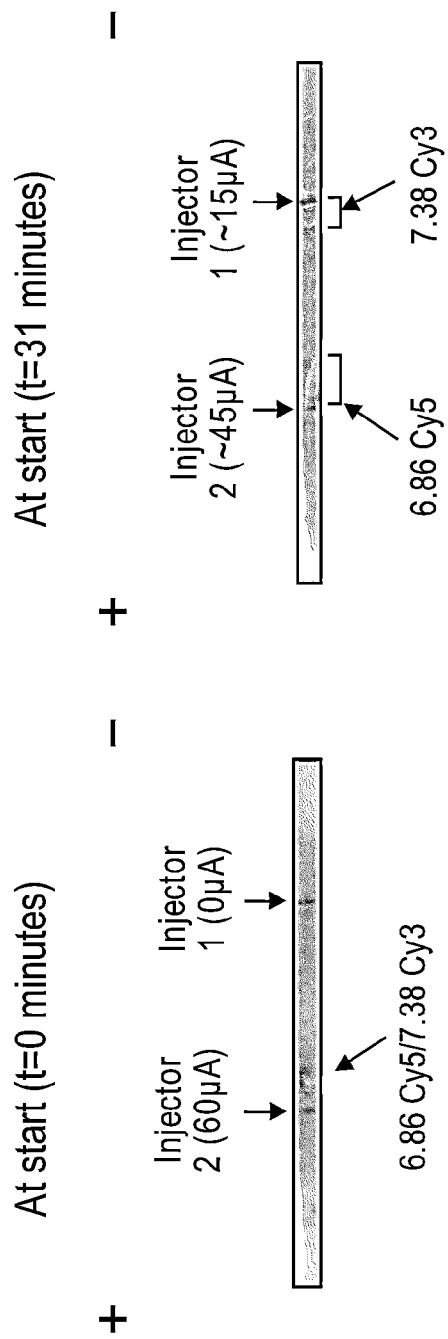
FIG. 10 shows separation of two different peptides having different pI.

Result:

6.86 Cy5 (pI ~6.8) was separated from 7.38 Cy3 (pI ~7.3). See, FIG. 10.

Example 3

Separation of dsDNA from Peptide/Protein

A mixture of dsDNA and 6.86cy3 peptide injected at the cathode end in a channel as used din Example 2, operated at 150V.

Buffer used: 4 mM Sodium Citrate, 4 mM Sodium Phosphate (dibasic), 4 mM Sodium Pyrophosphate, 13 mM Sodium Sulphate, pH adjusted to 8.5 (with $H_2SO_4$).

Figure 11A:
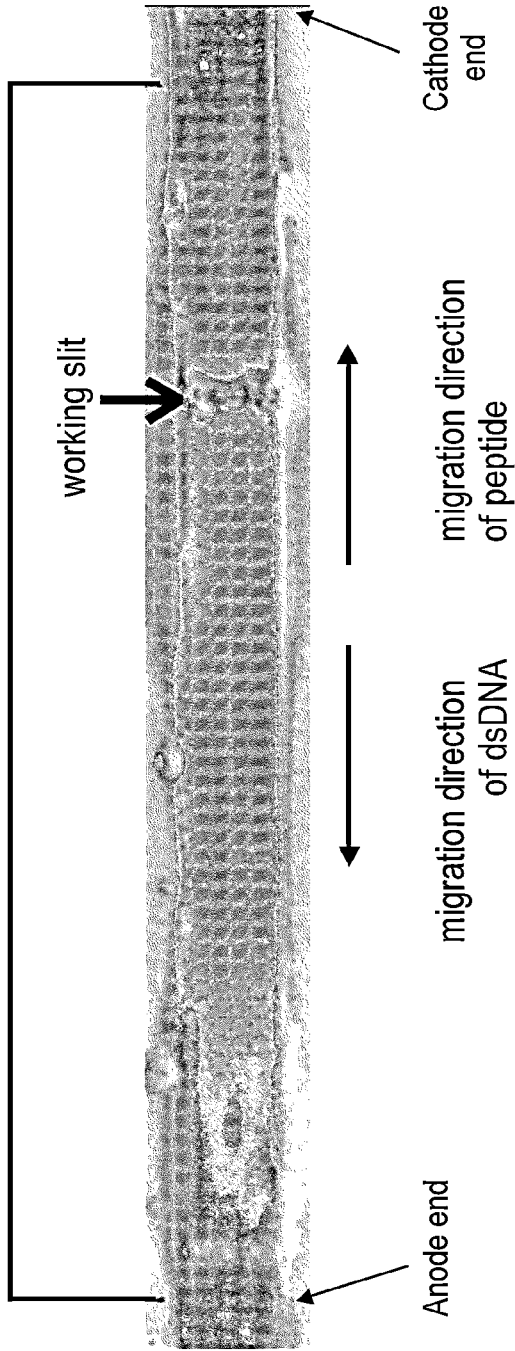
FIG. 11A-B shows separation of a peptide and dsDNA.
Figure 11B:
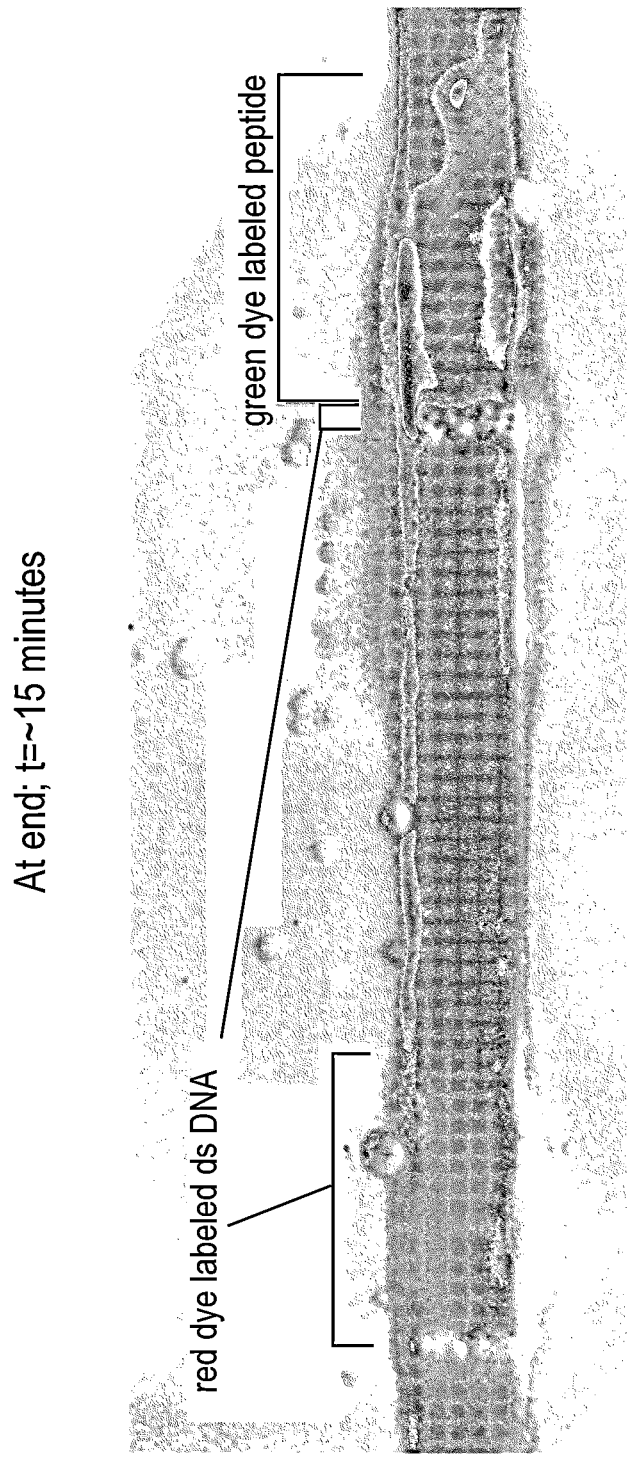

Result:

Separation of dsDNA from 6.86Cy3 peptide was achieved. See FIG. 11A-B.

Example 4

Focusing Mitochondria Based on pI

A band of cy3 fluorescent mitochondria was focused in a channel between H+ and OH-injectors. The running solution in the channel contained the following ingredients: 4 mM citrate, 4 mM phosphate, 4 mM pyrophosphate, 13 mM Na2SO4, 1% PVP40, 250 mM Sucrose, pH 7.5. The mitochondria was fluorescently labeled with JC-1. The channel had the following dimensions:

| Channel L/H/W in mm | Slit L/H/W In mm | Material | Channel volume (Vc; in μl) | Slit volume in μl (Vs; in μl) |
|---|---|---|---|---|
| 33.6 × 0.25 × 1 | 1 × 0.25 × 0.23 | PMMA | 8.4 | 0.0575 |

The focusing accrued in the following way: First, 200 volts were applied in the focusing channel, where the resulting electric field pointed from the proton injector to the hydroxyl injector. Then injection currents were applied, 50 μA and −50 μA in the proton and hydroxide injectors, respectively. Next, 10 μl of mitochondria solution were injected into the channel. Finally, after 2-3 minutes, the mitochondria were observed focusing in the pH step generated between the injectors.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method of purifying at least one cellular component from a biological sample comprising one or more cells or a lysate thereof, wherein the one or more cells or lysate thereof comprises a plurality of cellular components of the one or more cells, the method comprising,
   providing into a chamber the sample; and
   generating a pH gradient or pH step in the chamber with one or more proton injector(s) and/or hydroxide injector(s), such that at least two different cellular components from the plurality of cellular components are positioned in different positions in the chamber based on the isoelectric point (pI) of the at least two different components, thereby purifying at least one cellular component from a different cellular component,
   wherein the plurality of cellular components are electrophoretically moved through the inside of the chamber.

2. The method of claim 1, further comprising detecting the presence or quantity of at least one of the at least two components.

3. The method of claim 1, further comprising collecting the at least one of the at least two different cellular components, thereby purifying the at least one cellular component from the biological sample.

4. The method of claim 3, wherein the components are electrophoretically moved through the inside of the chamber in one path and at least some of the components are separately collected from an orifice in the chamber.

5. The method of claim 1, wherein the at least two different cellular components are positioned electrophoretically.

6. The method of claim 1, wherein the one or more cells are lysed in the chamber.

7. The method of claim 1, wherein the at least two different cellular components are selected from nuclei, DNA, RNA, peptide, and protein.

8. The method of claim 1, wherein the at least two different cellular components are different subcellular compartments and/or organelles.

9. The method of claim 1, wherein an agent having affinity for a target cellular component is linked to a position in the chamber and components of the cell lysate are moved to or past the agent, thereby binding the target cellular component to the agent.

10. A device or system for capturing a cell, cellular component, or virus from a biological sample, the device comprising, a chamber for containing a solution having a biological sample along an axis, wherein the chamber comprises one or more slit or other opening in the surface of the chamber in communication with one or more proton injector(s) or hydroxide injector(s), and wherein the chamber comprises an agent linked to a position in the chamber, wherein the agent has affinity for a target cellular component, cell, or virus;

an electrical source for applying an electric field in the injector(s) and optionally along the axis in the chamber;

the one or more proton injector(s) or hydroxide injector(s) for establishing a pH gradient along said axis in said chamber by injecting ion flows, capable of forming one or more pH steps in a pH gradient;

a controller which operates said one or more ion sources to adjust the pH gradient so as to induce positioning of charged components, cells or viruses along the axis in the chamber.

11. The device or system of claim 10, wherein the agent comprises an oligonucleotide.

12. The device or system of claim 11, wherein the oligonucleotide comprises a poly-T sequence sufficient to bind poly adenylated RNA.

13. A method for separating one or more target cell type or virus from at least one other cell type in a mixture and/or concentrating a target cell type or virus from a mixture, the method comprising providing into a chamber the mixture and buffered solution; and generating a pH gradient or pH step in the chamber with one or more proton and/or hydroxide injector, thereby positioning cells in the chamber based on the isoelectric point (pI) of the cells or viruses.

14. The method of claim 13, further comprising detecting the presence or quantity of cells or viruses at one position in the chamber.

15. The method of claim 13, further comprising collecting one or more cell or virus based on the one or more cell's or virus' pI.

16. The method of claim 15, wherein the cells or viruses are moved down the inside of the chamber in one path and at least some of the cells or viruses are separately collected from an orifice in the chamber.

17. The method of claim 16, wherein the cells or viruses are moved electrophoretically.

18. The method of claim 13, wherein the cells or viruses are positioned electrophoretically.

19. The method of claim 13, wherein an agent having affinity for a target cell or virus is linked to a position in the chamber and components of the mixture are moved to or passed the agent, thereby binding the target cell or virus to the agent.

* * * * *